(12) United States Patent
Baldo

(10) Patent No.: US 11,246,392 B2
(45) Date of Patent: Feb. 15, 2022

(54) ANHYDROUS DEODORANT AEROSOL EQUIPPED WITH A HOLLOW DISPENSING HEAD

(71) Applicant: L'OREAL, Paris (FR)

(72) Inventor: Francine Baldo, Sceaux (FR)

(73) Assignee: L'OREAL, Paris (FR)

( * ) Notice: Subject to any disclaimer, the term of this patent is extended or adjusted under 35 U.S.C. 154(b) by 176 days.

(21) Appl. No.: 15/534,159

(22) PCT Filed: Dec. 11, 2015

(86) PCT No.: PCT/EP2015/079506
§ 371 (c)(1),
(2) Date: Jun. 8, 2017

(87) PCT Pub. No.: WO2016/092109
PCT Pub. Date: Jun. 16, 2016

(65) Prior Publication Data
US 2019/0082808 A1  Mar. 21, 2019

(30) Foreign Application Priority Data

Dec. 12, 2014  (FR) ...................................... 1462379

(51) Int. Cl.

| | | |
|---|---|---|
| *A45D 34/04* | (2006.01) |
| *A61K 8/26* | (2006.01) |
| *A61K 8/31* | (2006.01) |
| *A61K 8/41* | (2006.01) |
| *A61Q 15/00* | (2006.01) |
| *A61K 8/04* | (2006.01) |
| *A61K 8/02* | (2006.01) |
| *B05B 1/06* | (2006.01) |
| *A61K 8/9794* | (2017.01) |
| *A61K 8/37* | (2006.01) |
| *A61K 8/49* | (2006.01) |
| *A61K 8/892* | (2006.01) |

(52) U.S. Cl.
CPC ............ *A45D 34/04* (2013.01); *A61K 8/0254* (2013.01); *A61K 8/046* (2013.01); *A61K 8/26* (2013.01); *A61K 8/31* (2013.01); *A61K 8/37* (2013.01); *A61K 8/416* (2013.01); *A61K 8/4973* (2013.01); *A61K 8/892* (2013.01); *A61K 8/9794* (2017.08); *A61Q 15/00* (2013.01); *B05B 1/06* (2013.01); *A45D 2200/057* (2013.01); *A61K 2800/31* (2013.01); *A61K 2800/612* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 3,792,068 A | 2/1974 | Luedders et al. | |
| 2005/0163737 A1* | 7/2005 | Lemoine ............ | A61K 8/4913 424/66 |
| 2010/0196484 A1* | 8/2010 | Aubrun ................... | A61K 8/19 424/489 |
| 2012/0171143 A1* | 7/2012 | Banowski ............... | A61K 8/86 424/65 |

FOREIGN PATENT DOCUMENTS

WO  WO2013102865 A1  7/2013

* cited by examiner

*Primary Examiner* — Robert A Wax
*Assistant Examiner* — Randeep Singh
(74) *Attorney, Agent, or Firm* — Polsinelli PC

(57) ABSTRACT

The present invention a device for dispensing a composition, comprising:
i) a dispensing head (1) intended to be fitted on a container that contains said composition, comprising:
a body (3) that is open at its two opposite axial ends,
an engaging part (10) that is open at its two opposite axial ends, at least partially defining at least one dispensing orifice (12), the cross section of the dispensing orifice being between 0.02 mm$^2$ and 0.5 mm$^2$,
ii) the anhydrous composition comprising, in particular in a physiologically acceptable medium:
a) at least one oily phase comprising at least one volatile hydrocarbon-based oil, and
b) at least one clay, and
c) at least one deodorant active agent, and
d) at least one propellant.
The present invention also relates to a method for the cosmetic treatment of body odor and optionally of human perspiration, which consists in applying to the surface of a keratin material a composition as defined above by means of the dispensing device defined above.

26 Claims, 8 Drawing Sheets

ANHYDROUS DEODORANT AEROSOL EQUIPPED WITH A HOLLOW DISPENSING HEAD

CROSS REFERENCE TO RELATED APPLICATIONS

Figure 1:
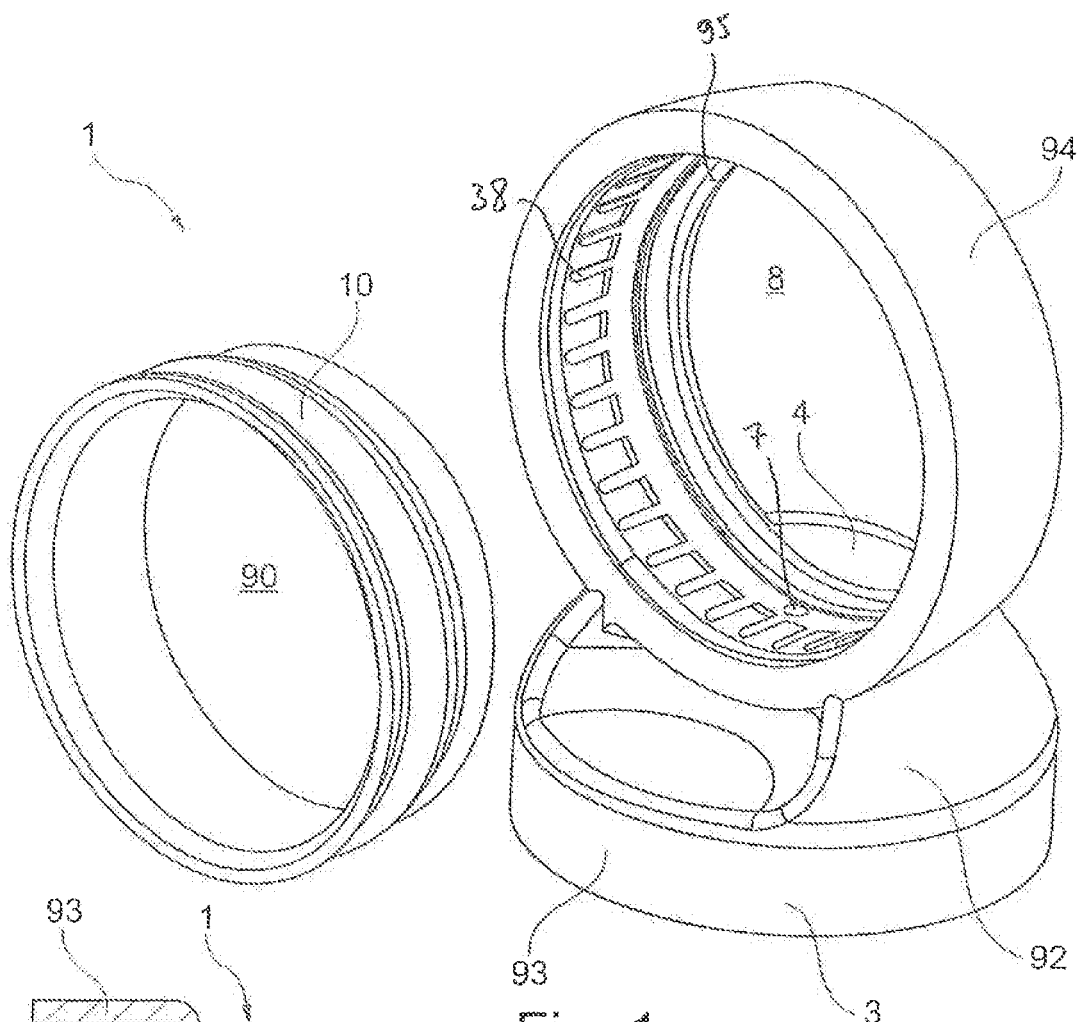

This application is a National Phase filing under 35 U.S.C. § 371 of PCT/EP2015/079506 filed on Dec. 11, 2015; and this application claims priority to Application No. 1462379 filed in France on Dec. 12, 2014 under 35 U.S.C. § 119. The entire contents of each application are hereby incorporated by reference.

The present invention concerns a device for dispensing a composition, comprising:
i) a dispensing head (1) intended to be fitted on a container that contains said composition, said device comprising:
 a body (3) that is open at its two opposite axial ends,
 an engaging part (10) that is open at its two opposite axial ends, at least partially defining at least one dispensing orifice (12), the cross section of the dispensing orifice being between 0.02 mm² and 0.5 mm²,
ii) the anhydrous composition comprising, in particular in a physiologically acceptable medium:
a) at least one oily phase comprising at least one volatile hydrocarbon-based oil, and
b) at least one clay, and
c) at least one deodorant active agent, and
d) at least one propellant.

The present invention also relates to a method for the cosmetic treatment of body odor and optionally of human perspiration, which consists in applying to the surface of a keratin material a composition dispensed by means of the dispensing device defined above.

Deodorant/antiperspirant aerosols are particularly desired by the consumer for their very good efficacy but they have a tendency to bring about stinging sensations or sometimes a feeling of dryness that may disturb the comfort of the user, especially in people with sensitive skin or who have shaved their armpits.

In the aerosol devices proposed to date for dispensing deodorant/antiperspirant products, many spray heads have been proposed, having one or several dispensing orifice(s). Numerous parameters should be taken into consideration when designing a spray head.

First of all, the spray generated should have the particle size distribution suitable for the application. In this respect, the size of the droplets should not be too small or too large.

Furthermore, the spray generated should be delivered at the flow rate required and the spray head should not subject the flow of product to an excessive pressure drop.

The form of the spray should likewise correspond to the intended application and thus make it possible, as the case may be, to cover a more or less extensive area. Finally, the spray head should be esthetically pleasing to the consumer, and its manufacture should be compatible with the requirements of large-scale production.

Application EP 1 052 023 A1 discloses a spray head comprising a dispensing orifice defined between a closure member having a frustoconical part and the body of the head. The closure member is opened by deformation of the frustoconical part, under the pressure of the product during dispensing. A conical and hollow spray is formed at least in the vicinity of the head.

Application WO 2011/065413 discloses various arrangements of spray heads in which a spray orifice is defined between a peripheral part and a central part which are connected together by bridges of material.

The invention aims to propose an aerosol device with a dispensing head that is very particularly suitable for spraying a deodorant or antiperspirant product without the drawbacks mentioned above in particular of preventing or substantially reducing the stinging sensations or feelings of dryness.

The invention also aims to propose an aerosol device with a spray head that produces a totally original visual effect with respect to that which exists currently.

The invention also aims to propose an aerosol device with a spray head that gives a sensation, on application, different from the sensations felt with the current devices.

Moreover, the spraying should be effective for the intended application.

In particular, in the field of deodorants or antiperspirants, spray heads are desired with which it is possible to precisely reach a given target.

There exists a need to increase the speed of application of a product by spraying without, however, increasing the risks of blockage related to the drying of the sprayed product.

The invention thus aims to further improve the known devices while making possible the use of manufacturing techniques having a cost compatible with large-scale distribution.

The present invention concerns a device for dispensing a composition, comprising:
i) a dispensing head (1) intended to be fitted on a container that contains said composition, said device comprising:
 a body (3) that is open at its two opposite axial ends,
 an engaging part (10) that is open at its two opposite axial ends, at least partially defining at least one dispensing orifice (12), the cross section of the dispensing orifice being between 0.02 mm² and 0.5 mm²,
ii) the anhydrous composition comprising, in particular in a physiologically acceptable medium:
a) at least one oily phase comprising at least one volatile hydrocarbon-based oil, and
b) at least one clay, and
c) at least one deodorant active agent, and
d) at least one propellant.

For the purposes of the invention, the term "anhydrous" is understood to mean a composition having a total water content of less than 3.0% by weight relative to the total weight of the composition, and preferably having a water content of less than 1% by weight relative to the total weight of the composition, or even that is free of water.

For the purposes of the present invention, the expression "physiologically acceptable medium" is understood to mean a medium that is suitable for the topical administration of a composition. A physiologically acceptable medium generally has no unpleasant odor or appearance, and is perfectly compatible with topical administration. In the present case, where the composition is intended for topical administration, i.e. by application at the surface of the keratin material under consideration, such a medium is considered in particular to be physiologically acceptable when it does not cause stinging, tightness or redness that is unacceptable to the user.

The expression "human keratin materials" is understood to mean the skin (of the body, face, contours of the eyes), head hair, eyelashes, eyebrows, body hair, nails, lips and mucous membranes.

The expression "deodorant active agent" is understood to mean any substance capable of reducing, masking or absorbing human body odors, in particular underarm odors.

The term "hydrocarbon-based oil" means an oil mainly comprising carbon and hydrogen atoms and optionally one or more functions chosen from hydroxyl, ester, ether and carboxylic functions.

The term "oil" means a fatty substance which is liquid at ambient temperature (25° C.) and atmospheric pressure (760 mmHg, i.e. $10^5$ Pa). The oil may be volatile or non-volatile.

For the purposes of the invention, the term "volatile oil" is intended to mean an oil that is capable of evaporating on contact with the skin or the keratin fiber in less than one hour, at ambient temperature and atmospheric pressure. The volatile oils of the invention are volatile cosmetic oils that are liquid at ambient temperature, with a non-zero vapor pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

Dispensing Device

In particular, the dispensing orifice is preferably defined between the body and the engaging part but may, alternatively, be defined entirely by the engaging part.

By virtue of the invention, a passage is formed through the dispensing head and more particularly through the body and the engaging part, allowing a flow of air to be established through the head when the product to be dispensed is emitted, and this can prove advantageous when the product is emitted in the form of a spray, allowing a current of air to be created through the head in order to accompany the flow of the spray.

In addition, the dispensing head has an appearance which contrasts clearly with the usual esthetics of known dispensing heads, and which proves to be particularly attractive to the consumer.

Furthermore, the passage through the head can be produced with dimensions sufficient to allow, if desired, a finger or a lock of hair to be inserted into this passage. This can make it easier to apply a product to the finger or the lock of hair.

If desired, the invention can also make it easier to produce a dispensing orifice having an annular section between the engaging part and the body, allowing the formation of a hollow spray. Alternatively, a plurality of dispensing orifices are formed between the body and the engaging part, for example in order to dispense the product in the form of a number of sprays or jets. The number of dispensing orifices may in particular be greater than or equal to 10, better still greater than or equal to 20, even better still greater than or equal to 30. The dispensing orifices each have for example a cross section greater than or equal to 0.003 $mm^2$, better still greater than or equal to 0.006 $mm^2$ and are preferably spaced apart from one another (measurement along a straight line between the barycenters of the orifices) by a distance of more than 1 mm.

In another variant, several dispensing orifices are formed entirely in the engaging part. The orifices may be constructed in such a way that the jet exiting from each orifice swirls, especially by virtue of at least two swirl ducts oriented tangentially around the axis of the orifice. The engaging part may have a U-shaped axial half-section. The body may have two concentric mounting skirts between which the engaging part is fastened. The body may comprise a crown into which the engaging part is inserted, the crown possibly bearing one or more reliefs defining, with the engaging part, ducts, especially swirl ducts, for supplying the dispensing orifice.

The body may define a housing that receives the engaging part, which is then called a core.

The one or more dispensing orifices may be open at rest. The expression "at rest" should be understood as meaning before the engaging part is exposed to the pressure of the product to be dispensed. Thus, in this case, one or more dispensing orifices are already formed and open when the product is sent into the head in order to be dispensed. Alternatively, the dispensing orifice is formed at the time the product is dispensed, by virtue for example of the elasticity of at least a portion of the body or of the engaging part, which deforms under the pressure of the product at the time it is dispensed.

By virtue of the invention, in the case of spraying, the spray can be emitted at a relatively high flow rate, if desired, while having a spray head which has a relatively simple design and functions reliably. In particular, the dispensing orifice may be produced with well-defined dimensions. In addition, the dispensing head may be esthetically pleasing to the consumer.

The body may have a first surface that flares toward the outside, or converges toward the outside, and the engaging part may have a second surface, opposite the first surface, that diverges toward the outside, or converges toward the outside. The first surface may be conical. The second surface may be conical, with the same angle as the first surface or with a greater or smaller angle.

A different angle that results in a narrowing of the space may lead to an acceleration of the jet before it exits, and this may be advantageous in the context of a spray.

There may be one or more than one dispensing orifice and it may have an annular shape or some other shape. The dispensing orifice may have a constant width in the circumferential direction. The one or more dispensing orifices may be defined between two concentric surfaces of revolution, for example in the form of cylinders of revolution.

The one or more dispensing orifices may have axial symmetry, preferably rotational symmetry, in particular around the dispensing axis. The dispensing axis is defined by the general direction in which the product is dispensed by the head.

The engaging part is preferably attached, thereby making it, and the body, easier to manufacture. Alternatively, the engaging part is molded as one part with the body, in particular in the case of the dispensing of a foam, it then being possible for the dispensing orifice to have a larger section than in the case of the spraying of a spray.

The space formed between the body and the engaging part is supplied by at least one supply duct, the section of which is preferably greater than that of the dispensing orifice, thereby making it easier to fill this space before the product emerges through the dispensing orifice.

A product distribution chamber may advantageously be formed, between the engaging part and the body, upstream of the dispensing orifice. This can make the emission of a homogeneous spray, in particular, easier.

The supply duct for the product may open into this chamber, which preferably has an annular shape. Its width, which corresponds to the gap between the engaging part and the body, is preferably greater than the maximum width of the passage, via which the distribution chamber communicates with the dispensing orifice.

At least one of the body and the engaging part, preferably the body, may have at least one relief for centering the engaging part in relation to the body, and preferably at least ten, better still at least twenty, and even better still at least forty reliefs. These reliefs may extend as far as the edge of the part in which they are produced so as to generate a multitude of orifices via which jets of product exit, the centering reliefs especially being oriented parallel to the dispensing axis or obliquely in the same circumferential direction around the axis, and optionally also possibly defining, between one another, sectional narrowings that cause the jets of product to be accelerated. This or these reliefs are preferably located set back from the dispensing orifice when it is desired to generate a spray in the form of a single jet. The reliefs can be produced on the body, being for example in the form of axial ribs that are distributed regularly around the entire surface of the body opposite the engaging part.

The centering reliefs may optionally ensure alone that the engaging part is held on the body. Alternatively, the engaging part is fixed to the body somewhere other than in the region of the centering reliefs, it being possible in this case for the centering reliefs to have or not have a function of holding the engaging part on the body.

Preferably, the engaging part is fixed in relation to the body. Alternatively, the engaging part is fixed in an adjustable manner in relation to the body, in order for example to allow the user to adjust the width of the dispensing orifice or to close the latter when not in use, for example by screwing it through a quarter turn, this screwing being accompanied by an axial movement of the engaging part in relation to the body.

The engaging part may lie flush with the front end of the body so as to generate a spray with an axis substantially parallel to the axis of the engaging part.

The engaging part may extend axially beyond the front end of the body by an amount lying between 0 and 1 mm, and better still between 0 and 0.5 mm. The spray may then diverge away from the axis of the engaging part.

The engaging part may be axially set back from the front end of the body by an amount lying between 0 and 1 mm, and better still between 0 and 0.5 mm. The spray may then converge toward the axis of the engaging part.

Advantageously, the dispensing orifice has a triangular cross section.

More advantageously, the engaging part at least partially defines a plurality of dispensing orifices, the sum of the cross sections of the dispensing orifices being between 0.02 mm$^2$ and 0.5 mm$^2$.

More advantageously still, the number of dispensing orifices is greater than or equal to 5, preferably greater than or equal to 10.

Preferably, the cross section of the dispensing orifices is between 0.03 mm$^2$ and 0.4 mm$^2$, preferably between 0.05 mm$^2$ and 0.5 mm$^2$, and preferably between 0.05 mm$^2$ and 0.4 mm$^2$.

The invention makes it possible to easily produce, if desired, a dispensing orifice having a circular internal contour. The inside diameter of the passage formed through the head is for example greater than or equal to 10 mm, better still greater than or equal to 15 mm, 20 mm or 30 mm. When the passage does not have a circular section, the "inside diameter" designates the diameter of the largest circle inscribed in this passage.

The head may comprise at least two housings and two engaging parts that are disposed in the housings and each define with the body, at rest, a dispensing orifice according to the invention. The dispensing axes may then be parallel or not parallel, intersecting or not intersecting, for example converging toward one another.

The dispensing orifice may have, in axial half section, an axis that converges or diverges in relation to the spraying direction.

A further subject of the invention, according to another of its aspects, is a container provided with a dispensing head according to the invention.

The invention also relates to a device for dispensing a composition, said device comprising:
i) a dispensing head intended to be fitted on a container that contains said composition to be dispensed,
the dispensing head comprising:
 a body that is open at its two opposite axial ends,
 an engaging part that is open at its two opposite axial ends, at least partially defining a dispensing orifice, and
ii) the anhydrous composition comprising, in particular in a physiologically acceptable medium:
a) at least one oily phase comprising at least one volatile hydrocarbon-based oil, and
b) at least one clay, and
c) at least one deodorant active agent, and
d) at least one propellant.

The invention also relates to a device for dispensing a composition, said device comprising:
i) a dispensing head intended to be fitted on a container that comprises a valve rod or pump rod, the dispensing head comprising:
 a body provided with an end piece for connecting to the valve rod or pump rod,
 a part attached to the body, at least partially defining a dispensing orifice having an annular section at rest or several dispensing orifices distributed around a dispensing axis (Z);
the head not being a through-head along the dispensing axis (Z);
the body being closed along the dispensing axis (Z) and said part being of annular shape, or
the body having a through-opening along the dispensing axis (Z) and said part closing this opening;
ii) a composition comprising, in particular in a physiologically acceptable medium:
a) at least one oily phase comprising at least one volatile hydrocarbon-based oil, and
b) at least one clay, and
c) at least one deodorant active agent, and
d) at least one propellant.

The container may be a pressurized container, provided for example with a hollow valve rod inserted into a housing in the head that is suitable for holding said rod.

Figure 2:
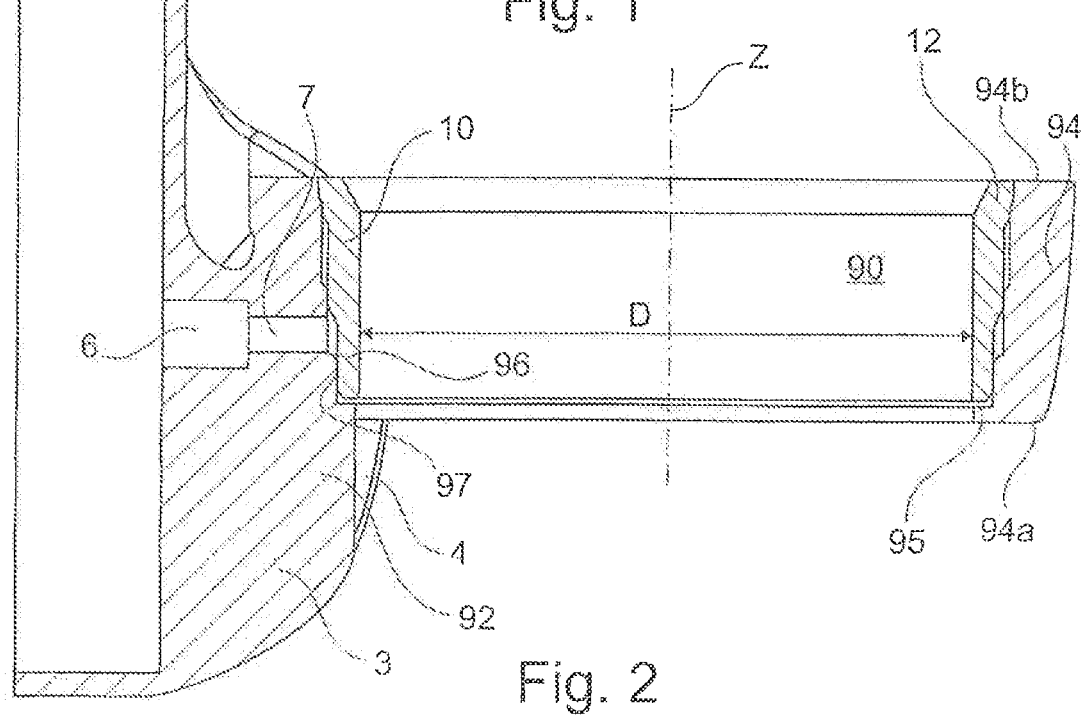
Figure 3:
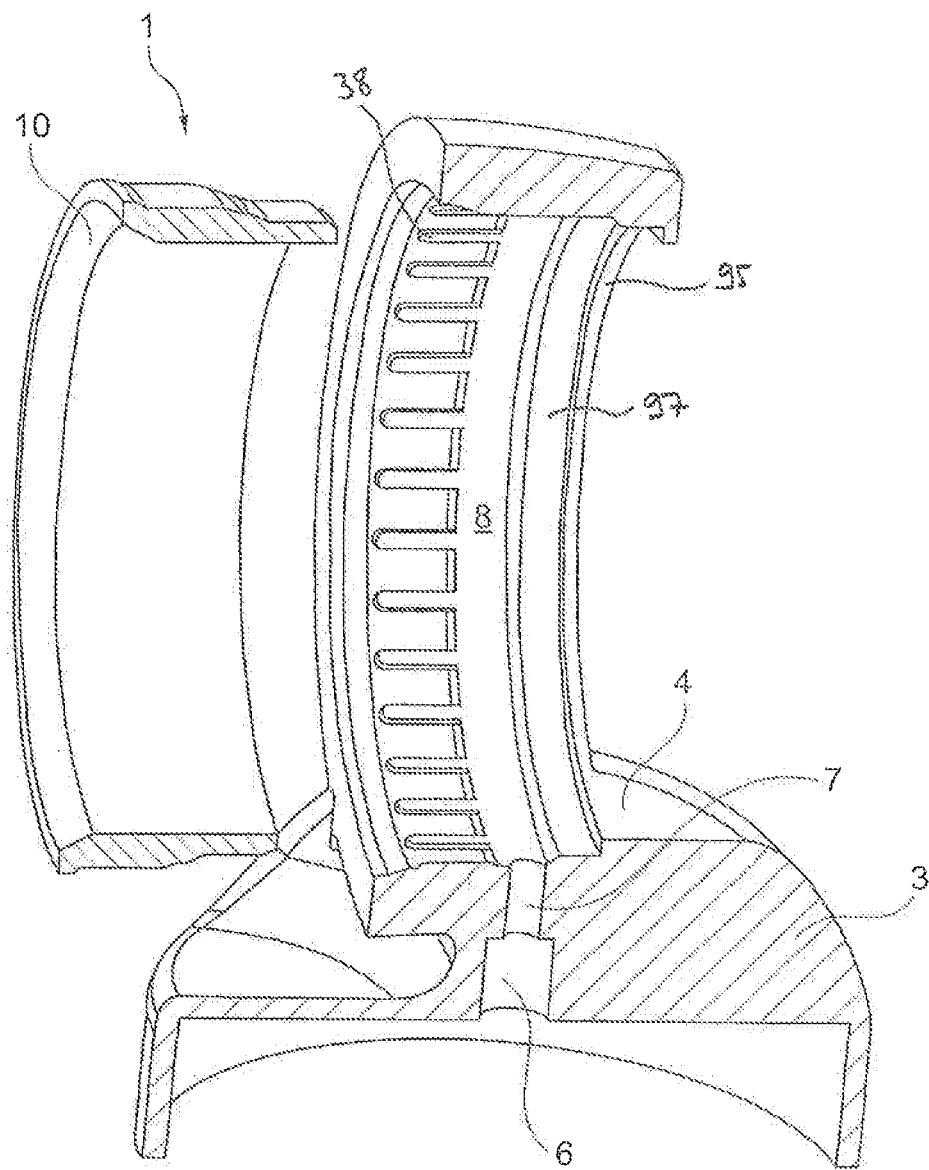
Figure 4B:
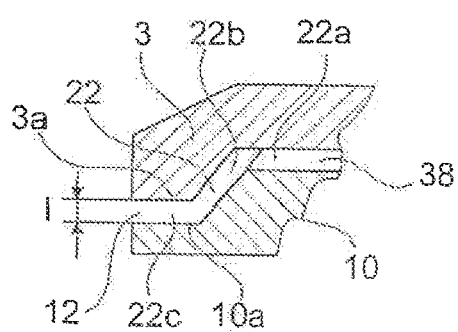
Figure 4C:
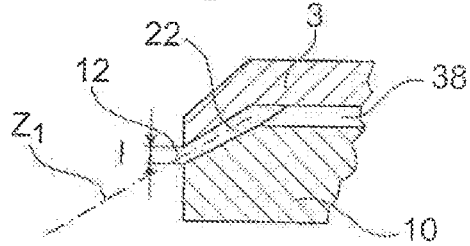
Figure 4F:
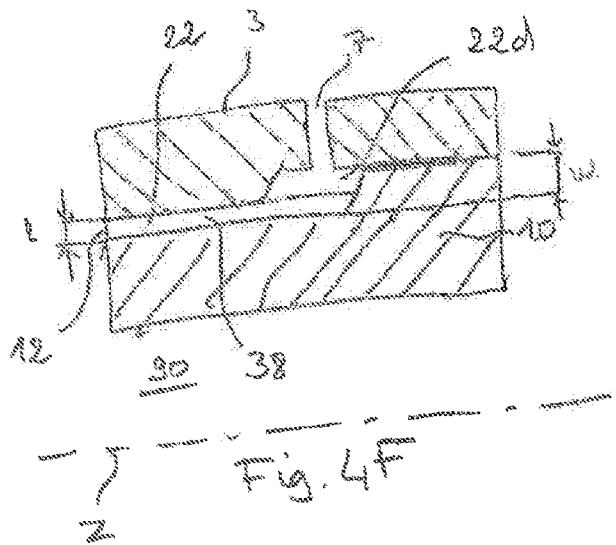
Figure 4A:
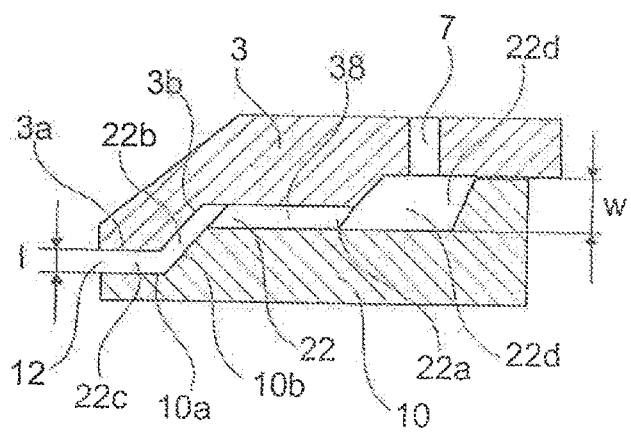
Figure 4E:
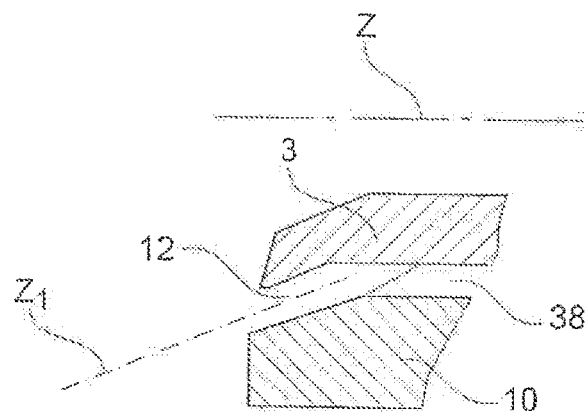
Figure 4D:
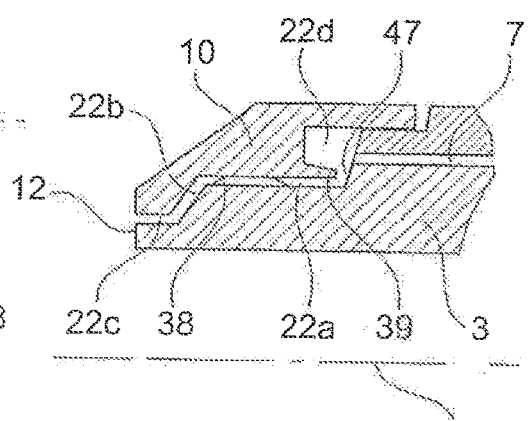
Figure 5:
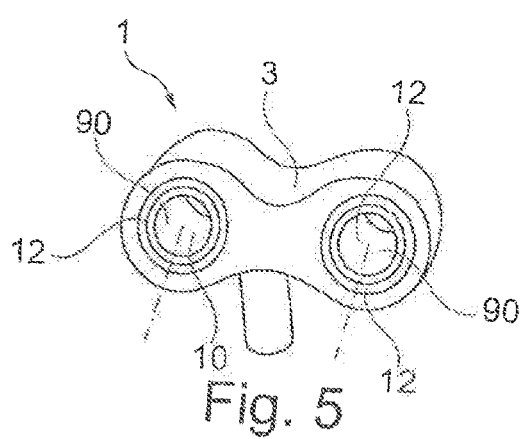
Figure 6:
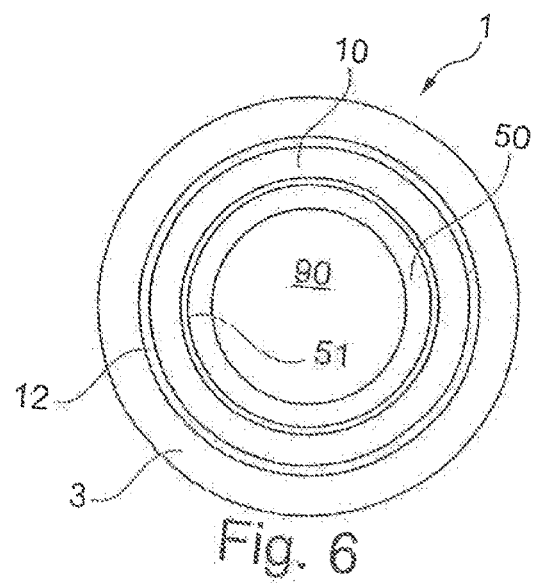
Figure 7:
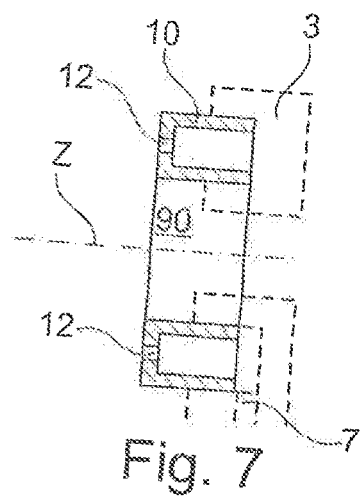
Figure 8A:
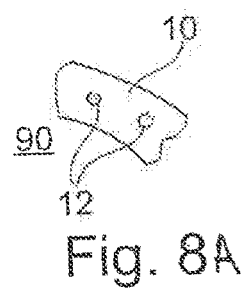
Figure 8B:
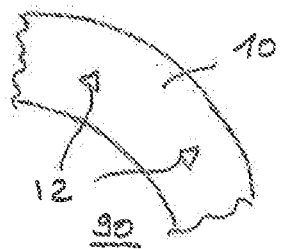
Figures 9, 10A:
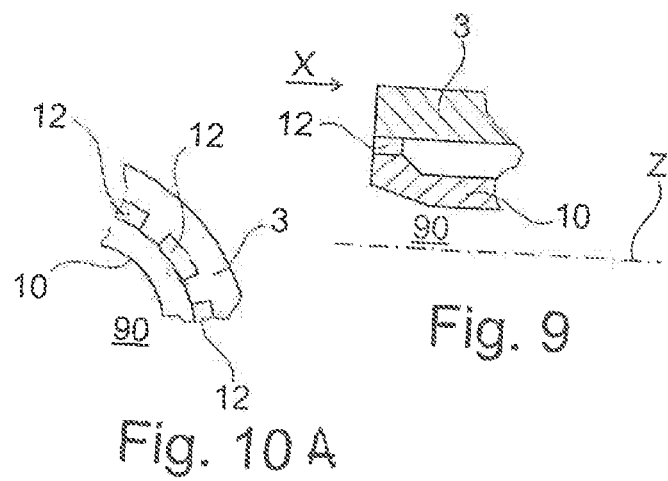
Figure 10B:
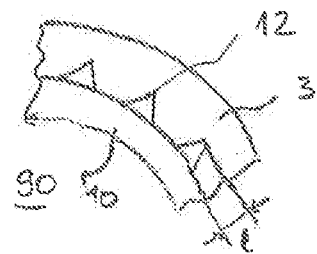
Figure 11:
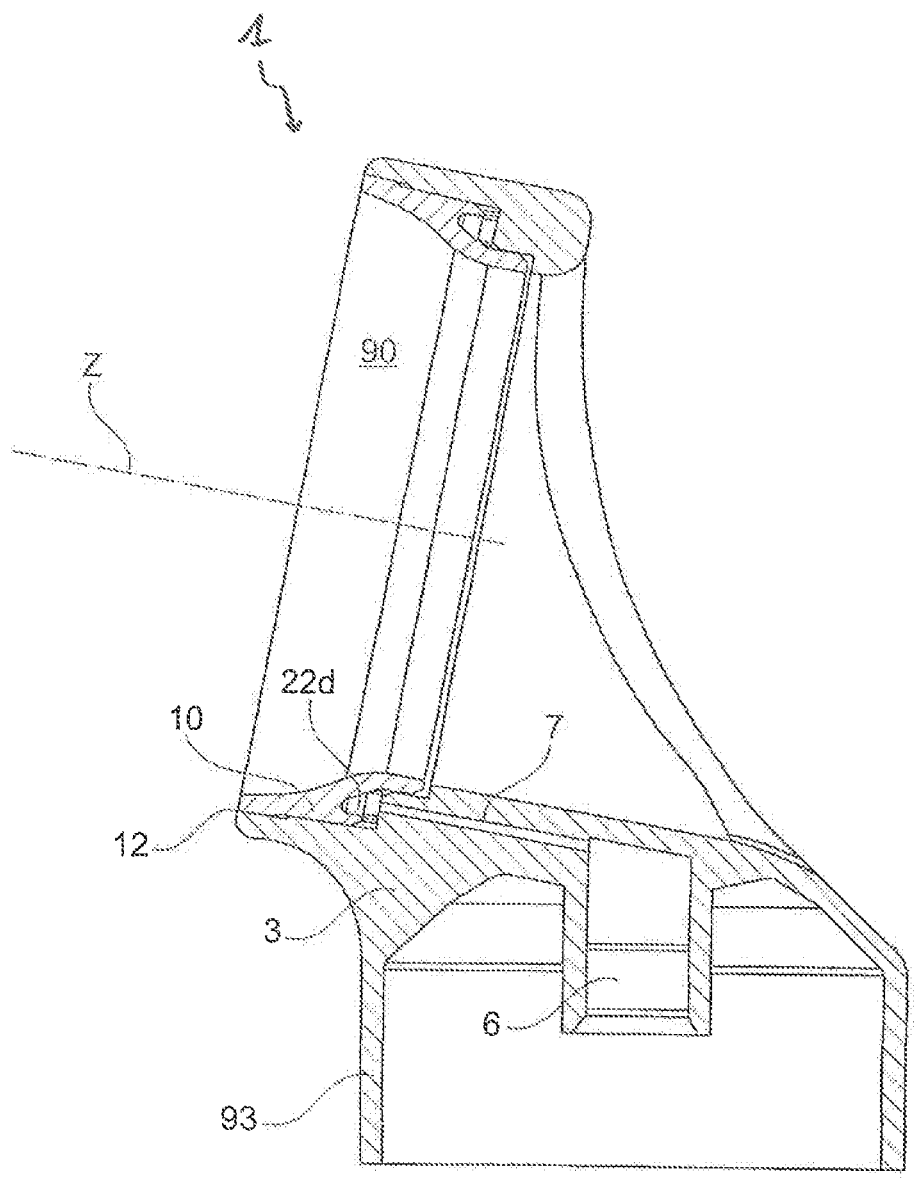
Figures 13A, 13B, 13C:
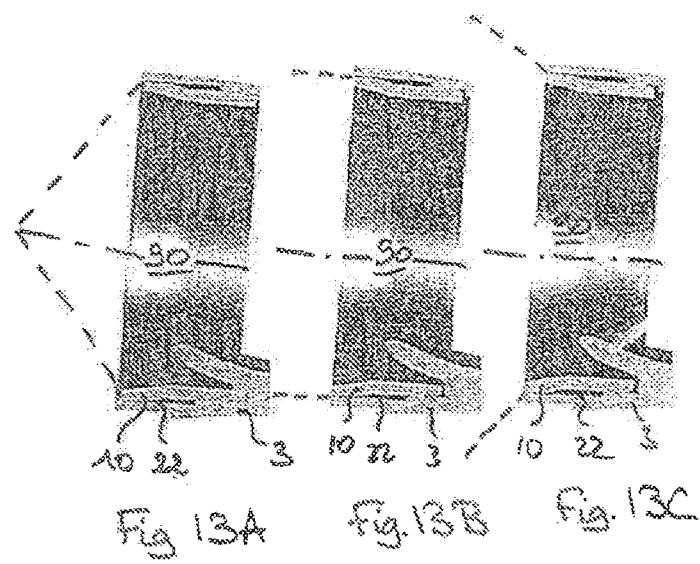
Figure 12A:
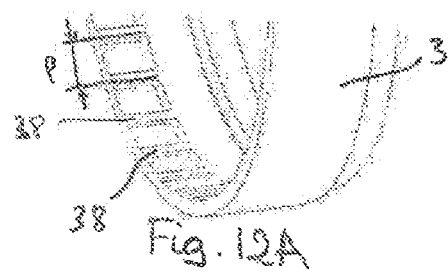
Figure 12B:
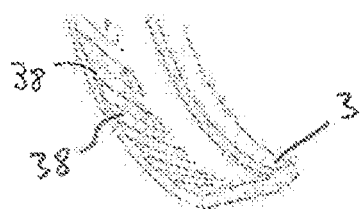
Figure 12C:
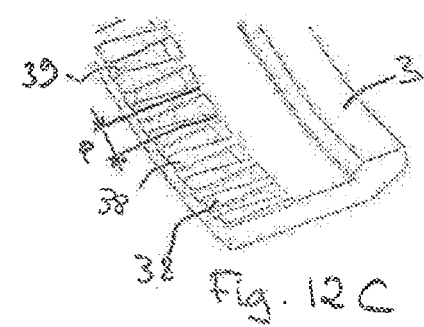
Figure 14:
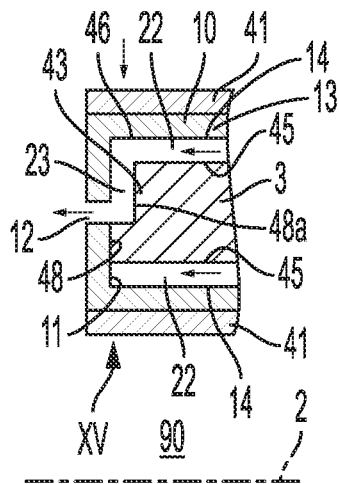
Figure 15:
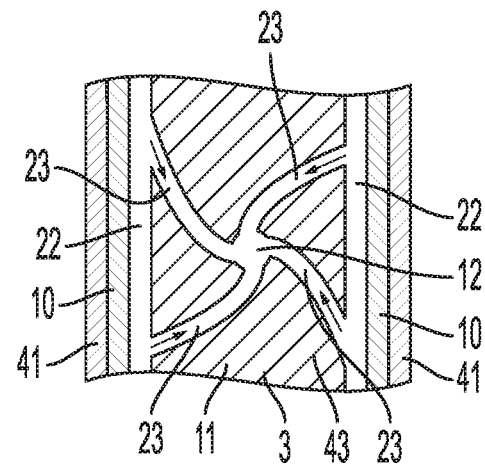
Figure 16:
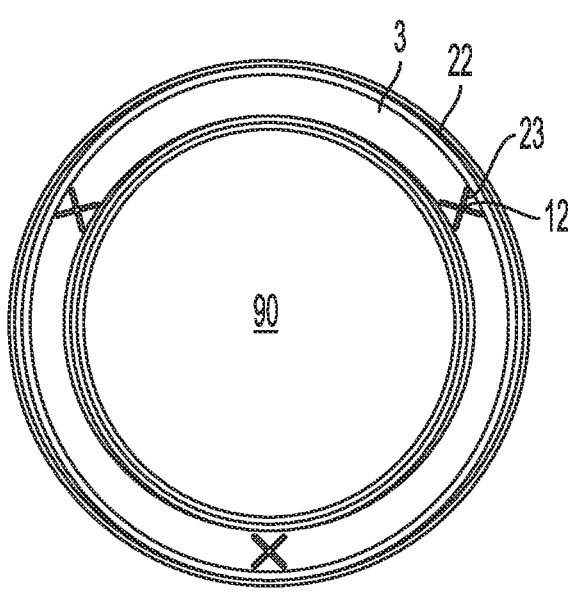
Figure 17:
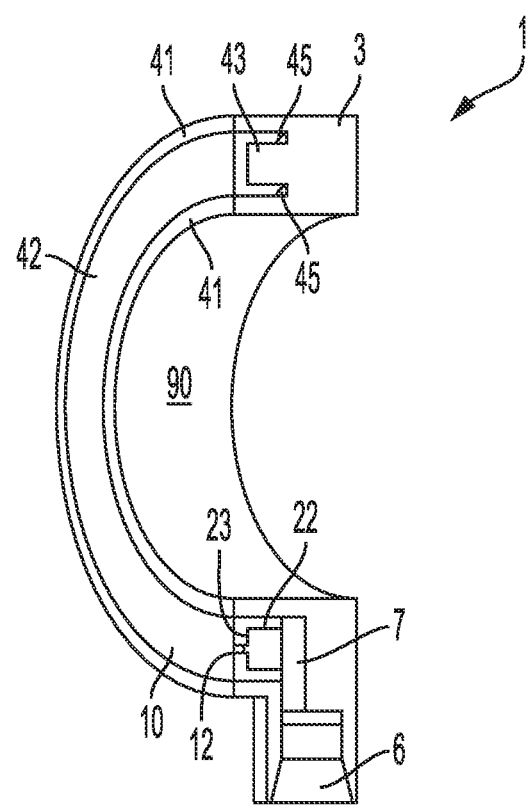

The invention may be better understood from reading the following detailed description of non-limiting implementation examples thereof and from examining the appended drawing, in which:

FIG. 1 schematically shows a perspective view of an example of a dispensing head produced in accordance with the invention, before the engaging part is fitted on the body of the head, FIG. 2 shows the dispensing head after the engaging part has been fitted in the body, FIG. 3 is a view similar to FIG. 1 in partial section, FIGS. 4A to 4F illustrate various arrangements, among others, of the engaging part and the body, FIG. 5 illustrates the possibility of producing the dispensing head with two dispensing orifices according to the invention, FIG. 6 shows a front view of a dispensing head having concentric dispensing orifices, FIG. 7 is an axial section through an embodiment variant of the engaging part, FIGS. 8A and 8B are various examples of configurations of the engaging part from FIG. 7 as a partial front view, FIG. 9 is a partial axial section through a variant embodiment of the dispensing orifice, FIGS. 10A and 10B are front views along X of various examples of configuration according to FIG. 9, FIG. 11 is a view similar to FIG. 2 of an embodiment variant of the head, FIGS. 12A to 12C illustrate various examples of arrangements of the reliefs on the body, FIGS. 13A to 13C illustrate various examples of configurations of the engaging part with respect to the body, FIG. 14 is a partial axial section through an embodiment variant of the dispensing orifice, FIG. 15 is a section along XV from FIG. 14, FIG. 16 is an exemplary embodiment of the body according to FIG. 14, and FIG. 17 is a cutaway perspective view of an example of a dispensing head according to the configuration from FIG. 14.

In the drawing, the actual respective proportions of the various constituent elements have not always been respected, for the sake of clarity.

The dispensing head 1 shown in FIGS. 1 to 3 is intended to be fitted on a container (not shown) provided with a hollow valve rod or hollow pump rod, through which the product to be dispensed that is contained in the container is conveyed toward the head 1.

The container may in particular be a pressurized container of the aerosol can type, containing a propellant gas such as compressed air, for example, or a liquefied gas.

The container may be provided with a valve and the valve may be opened for example by pressing the hollow rod or alternatively by tilting the latter. When the container is provided with a pump, the pump may be actuated for example by pressing the hollow rod along its longitudinal axis.

The head 1 comprises a body 3 which may be produced in an integral manner by molding a single part or may comprise a plurality of elements produced separately and joined together.

The dispensing head 1 may comprise, as can be seen in FIG. 2, a housing 6 intended to engage with the hollow rod in order to allow the product delivered through the latter to reach a supply duct 7 which opens into a housing 8 in the body 3. The housing 6 has a dimension adapted to the outside diameter of the rod, so as to obtain a sealed fit of the rod in the housing 6, in order that the product delivered through the rod passes entirely into the supply duct 7. The latter is for example coaxial with the rod of the container but could be oriented in some other way and have for example a plurality of differently oriented portions.

An engaging part 10, called core in the following text when it is inside the body, is fixed in the housing 8 and defines for example with the body 3 a dispensing orifice 12 having an annular section, as illustrated.

The expression "annular section" should be understood within the meaning of the present invention as meaning any section that follows a closed contour, whether this contour is circular, elliptical, polygonal or some other shape.

Passing axially through the core 10 is an opening 90, the inside diameter D of which may be relatively large, for example greater than or equal to 10 mm, better still 15, 20 or 30 mm.

The opening 90 helps to give the head a particularly esthetic appearance. In addition, the opening 90 can allow air to flow through the head under the entrainment effect of a spray emitted through the dispensing orifice 12. This can help to increase the range of the spray and can increase the freshness effect provided thereby, if need be.

The opening 90 may also allow a finger or a lock of hair to be inserted through the head, and this can make it possible to apply a product in a single movement over the entire circumference of the element inserted through the head. This can be an advantage for applying for example an antiseptic or care product to a finger or for treating a lock of hair.

The dispensing axis Z may be perpendicular to the longitudinal axis X of the container on which the head is fitted, as illustrated.

The head 1 comprises a base 92 which defines a surface 4 which the user can press in order to bring about dispensing.

The bottom of the base 92 can be extended by an enclosing skirt 93 which covers the upper part of the container.

The housing 8 which receives the core 10 is defined by a crown 94 of axis Z, the lower side of which is joined to the base 92. The supply duct 7 passes through the base 92 and leads into the housing 8 at a distance from the axial ends, along the axis Z, of the crown 94, being preferably closer to the rear end 94a than to the front end 94b, as can be seen in FIG. 2.

The body 3 may have, as illustrated, a shoulder 95 close to the rear end 94a, against which the core 10 can come into axial abutment, if need be, at the end of its fitting.

The core 10 and the housing 8 may have annular surfaces 96 and 97, in sealed contact, in order to close the space formed between the core 10 and the body 3 at the rear of the supply duct 7.

Preferably, the circumferential width l of the dispensing orifice 12, around the spraying direction Z, is constant. If this width l varies, for example so as to take into account the possibly non-uniform pressure drop experienced by the flow of product upstream of the dispensing orifice 12, this does not depart from the scope of the present invention. This non-uniform pressure drop results for example from the geometry of the space between the core and the body, in particular the presence of angles or intersections. By varying the width l, it is possible to ensure that the product can emerge more easily at the point where this pressure drop is greatest, if a spray which is as homogeneous as possible is desired.

The width l of the dispensing orifice is for example between 0.01 mm and 2 mm.

The core 10 can be fixed to the body 3 in various ways. In the example illustrated in FIGS. 1 to 3, the core 10 is retained on the body 3 by friction.

In the example illustrated, the core 10 is produced separately from the body 3 and is attached to the latter. The core 10 can be produced from the same thermoplastic material as the body 3 or alternatively from a different thermoplastic material. It is also possible to use a metal material to produce the core 10.

Axial ribs 38 are formed on the internal circumference of the housing 8, as can be seen in particular in FIGS. 1 and 3, in order to center the core 10 in the housing 8. The centering reliefs 38 may be, as illustrated in FIGS. 12A to 12C, parallel or oblique in the direction circumferential to the axis Z, or curved. Each relief 38 may have, when seen in a top view, a contour that is polygonal, in particular rectangular or trapezoidal, or that has a shape that is flared in the direction of the dispensing edge. Two centering reliefs 38 may define, between one another, a narrowing 39 in the vicinity of the dispensing orifice so as to accelerate the fluid via the Venturi effect. The number of centering reliefs 38 is preferably at least 10, better still 20, even better still 40.

The space 22 formed between the core 10 and the body 3 may have the configuration illustrated schematically in FIG. 4A, and open onto the dispensing orifice 12 by way of an annular terminal portion 22c formed between two surfaces 3a and 10a which are in the form of cylinders of revolution about the axis Z.

The terminal wall 22c is attached to a proximal portion 22a by way of an inclined intermediate portion 22b formed between opposite surfaces 3b and 10b.

The centering reliefs 38 extend in the proximal portion 22a. The latter is supplied with product via the distribution chamber 22d.

When the user actuates the dispensing head 1, the product passes through the supply duct 7 into the space 22 between the core 10 and the body 3 and can be delivered in the form of a spray through the dispensing orifice 12.

In the example in FIGS. 1 to 3, the spray is continued angularly around the dispensing axis on account of the absence of contact between the core 10 and the body 3 in the region of the dispensing orifice 12. Specifically, the bearing region or regions between the core 10 and the body 3 are for example located, as illustrated, set back from the dispensing orifice 12 by a distance (measured along the dispensing axis Z) of at least 0.5 mm.

The spray may be discontinuous angularly around the dispensing axis on account of the presence, in particular at the reliefs 38, of contact between the core 10 and the body 3 where the product emerges.

Preferably, the cross section of the supply duct 7 is greater than the section of the dispensing orifice 12 so as to allow the space located upstream of the dispensing orifice to be filled rapidly with the product, this being able to help to form a homogeneous spray right from the start of spraying.

The distribution chamber 22d formed upstream of the space 22a in which the centering reliefs 38 extend receives the product delivered through the supply duct 7.

The width ω of the distribution chamber 22d is greater than that l of the terminal portion 22c which opens onto the dispensing orifice 12.

The distribution chamber 22d improves the distribution of the product before the latter reaches the narrowest portions of the passage through which the product is evacuated.

FIGS. 4B and 4C illustrate different other examples of possible configurations for the space 22 formed between the core 10 and the body 3 for the product to flow to the dispensing orifice.

In the example in FIG. 4B, the space 22 formed between the core and the body comprises a proximal portion 22a in which the centering reliefs 38 of the core 10 extend in relation to the body 3, extended by an intermediate portion 22b which forms an angle with the spraying direction Z, for example a re-entrant angle. This intermediate portion 22b can be attached to a terminal portion 22c, which opens onto the dispensing orifice 12, this terminal portion being defined for example, as illustrated, between two surfaces 3a and 10a, in the form of cylinders of revolution, parallel to the dispensing direction Z. The variant in FIG. 4B does not have a distribution chamber.

In the variant in FIG. 4C, the terminal portion 22c communicates directly with that portion 22a in which the centering reliefs 38 extend. The terminal portion 22c forms, for example, an angle with the dispensing direction Z. Thus, in axial half section, the axis $Z_1$ of the orifice 12 is for example convergent, as illustrated.

In the variant in FIG. 4D, the engaging part 10 is outside the body 3. The engaging part 10 is fixed to the body 3 so as to form with the latter the distribution chamber 22d, facing the supply duct 7. The portions 22a, 22b and 22c allow the product to be conveyed to the dispensing orifice 12.

The supply duct 7 opens for example into the distribution chamber 22d via a portion oriented parallel to the dispensing axis Z.

Centering reliefs 38 are produced for example on the body 3. The engaging part 10 can be produced, as illustrated, with an annular lip 39 which partially delimits the distribution chamber 22d and forms a narrowing 47 of the section between the chamber 22d and the portion 22a.

FIG. 4E illustrates the possibility of having an angle which is divergent between the axis $Z_2$, in axial half section, of the orifice 12 and the dispensing axis.

In the variant in FIG. 4F, the possibility of having no angle between the dispensing axis and the axis Z of the engaging part 10 is illustrated. The supply duct 7 for example opens onto a distribution chamber 22d. The product is conveyed toward the dispensing orifice 12 via ducts 22 comprising reliefs 38. The reliefs 38 extend as far as the edge of the dispensing orifice 12 and define a plurality of orifices allowing the product to be delivered in the form of a plurality of jets.

The invention is not limited to a dispensing head comprising only one dispensing orifice 12 produced in accordance with the invention.

By way of example, FIG. 5 illustrates a dispensing head 1 which comprises two dispensing orifices 12.

When there are a plurality of dispensing orifices, these may be distributed in multiple ways on the dispensing head. For example, the spraying axes are parallel, or form an angle, in that, for example, they intersect.

FIGS. 7, 8A and 8B illustrate the possibility for the dispensing head to have a plurality of dispensing orifices 12 formed entirely in the core 10 in order to dispense the product in the form of a plurality of jets for example. The dispensing orifices 12 may have many shapes when observed along their transverse axis, especially being circular or triangular, as illustrated in FIGS. 8A and 8B. The dispensing orifices 12 may be cut into the core 10, for example by laser cutting.

The core 10 may have a U-shaped axial half-section, as illustrated in FIG. 7. The body 3 may comprise two concentric mounting skirts 41 which define between them a space for mounting the core 10, and may comprise, at its center, a crown 43 serving to support the engaging part 10. The skirts 41 define, with the crown 43, two annular ducts 45 into which the arms of the U fit. The crown 43 may have, for each orifice 12, two ducts 22 for supplying liquid to this orifice 12.

During mounting, as illustrated in FIGS. 14 and 17, the core 10 may bear against the pad 43, the end face 48 of the crown 43 making contact with the inner face 11 of the core 10. The arms of the U of the core 10 are fixed in the ducts 45, the inner face 46 of the mounting skirts 41 making contact with the face 13 of the core 10. The inner faces 14 of the arms of the U and the lateral surfaces 49 of the crown 43 may define, between one another, the ducts 22 for supplying liquid to the dispensing orifice 12. The crown 43 may have, especially in the form of impressions, on its outer face 48, supply ducts 23 allowing the liquid to pass from the supply ducts 22 to the dispensing orifice 12.

The supply ducts 22 open, upstream of the dispensing orifices 12, onto the supply ducts 23, which lead to the dispensing orifice 12. The supply ducts 23 generate, via their orientation relative to the dispensing orifice, a swirling flow at the outlet of the dispensing orifice 12. This configuration is more particularly useful in the case of a non-liquefied carrier gas.

In one variant, the supply ducts 22 may take the form of impressions on the lateral surface 49 of the body and/or on the inner faces 14 of the core 10.

In another variant (not shown), the core 10 possesses, especially in the form of impressions on its inner face 11, supply ducts 23, the end face 48 of the crown 43 possibly being smooth.

In a variant, the crown 43 is not circumferentially continuous and defines pads. The pads are placed upstream of the dispensing orifices 12 and may possess, upstream of the dispensing orifices 12, supply ducts 22 and 23 such as described above.

In the variant in FIGS. 4F, 9 and 10, the dispensing orifices 12 are formed between the core 10 and the body 3, being for example distributed all around the spraying axis Z. The core 10 or the body 3 may have centering reliefs 38 that circumferentially bound the dispensing orifices 12. The centering reliefs 38 may, as illustrated in FIGS. 12A to 12C, extend as far as the edge of the core 10 over its entire periphery and define, between one another, dispensing orifices 12. The number of dispensing orifices 12 is preferably at least 10, better still 20, even better still 40. The cross section of a dispensing orifice 12 is for example greater than 0.003 mm$^2$. The dispensing orifices 12 are preferably spaced apart by a space of at least 1 mm, which is the same as the pitch p between the centering reliefs. As illustrated in FIGS. 10A and 10B, the dispensing orifices 12 can have a polygonal cross section, especially a triangular cross section.

The core 10 may, as illustrated in FIG. 13A, be set back relative to the body by an amount lying between 0 and 1 mm, better still between 0 and 0.5 mm. The body 3 protrudes into the dispensing orifice and may generate a convergent spray.

The core 10 may, as illustrated in FIG. 13B, lie flush with the body 3. The spray may then be straight.

The core 10 may extend, as illustrated in FIG. 13C, forward, relative to the body 3 by an amount lying between 0 and 1 mm, better still between 0 and 0.5 mm. The spray may then be divergent.

If an additional dispensing orifice is provided, for example by attaching inside the core 10 a second core 50 which defines with the first core 10 a second dispensing orifice 51 which is coaxial with the first dispensing orifice, as illustrated in FIG. 6, this does not depart from the scope of the present invention. A passage 90 continues to be formed through the dispensing head.

The dispensing orifice may be supplied with more than one product.

The dispensing head may be supplied with two products which are dispensed through separate dispensing orifices.

It is possible for the axis Z not to be perpendicular to the axis of the rod of the container on which the head is fitted, as illustrated in FIG. 11. In this example, the axis Z is oriented upward when the container is vertical with the dispensing head at the top.

The supply duct 7 can be oriented substantially parallel to the dispensing axis Z, at least in the case of the portion which opens out facing the engaging part 10. The latter may be produced with an annular lip 39 which defines a narrowing of the section 47.

The configuration may be similar to that in FIG. 4D apart from the fact that the engaging part 10 is outside the body 3 in the example in FIG. 4D and inside it in the example in FIG. 11.

The dispensing head may be arranged so as to allow a protective cap to be fitted and to comprise, if need be, an on/off system that makes it possible to prevent the actuation of the device when the dispensing head is in a certain position with respect to the container or when a locking element of the dispensing head is in a certain position in relation to the latter.

In variants which are not illustrated, the dispensing orifice is formed between a body and an engaging part, the body being radially on the inside with respect to the engaging part, the supply duct for the product passing through the body. All of the features described with reference to the figures can be found in variants in which the body is radially on the inside with respect to the engaging part.

Composition

Deodorant Active Agents

Among the deodorant active agents, mention may in particular be made of antiperspirant active agents.

The expression "antiperspirant active agent" is understood to mean any aluminum salt or complex which, by itself alone, has the effect of reducing the flow of sweat, of reducing the sensation on the skin of moisture associated with human sweat and of masking human sweat.

According to one particular embodiment of the invention, the deodorant active agent present in the composition is an antiperspirant active agent.

Among the deodorant active agents that can be used according to the invention, mention may be made of antiperspirant or astringent active agents. They are preferably chosen from aluminum and/or zirconium salts; complexes of zirconium hydroxychloride and of aluminum hydroxychloride with an amino acid, such as those described in patent U.S. Pat. No. 3,792,068, commonly known as "ZAG complexes". Such complexes are generally known under the name ZAG (when the amino acid is glycine). ZAG complexes ordinarily have an Al/Zr quotient ranging from about 1.67 to 12.5 and a metal/Cl quotient ranging from about 0.73 to 1.93. Among these products, mention may be made of aluminum zirconium octachlorohydrex GLY, aluminum zirconium pentachlorohydrex GLY, aluminum zirconium tetrachlorohydrate GLY and aluminum zirconium trichlorohydrate GLY.

Among the aluminum salts, mention may be made of aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, alum salts, aluminum sulfate, aluminum zirconium octachlorohydrate, aluminum zirconium pentachlorohydrate, aluminum zirconium tetrachlorohydrate, aluminum zirconium trichlorohydrate and more particularly the aluminum chlorohydrate sold by the company Reheis under the name Microdry Aluminum Chlorohydrate® or by the company Guilini Chemie under the name Aloxicoll PF 40. Aluminum and zirconium salts are, for example, the product sold by the company Reheis under the name Reach AZP-908-SUF®, "activated" aluminum salts, for example the product sold by the company Reheis under the name Reach 103 or by the company Westwood under the name Westchlor 200.

Among the antiperspirant active agents, use will more particularly be made of aluminum chlorohydrate, aluminum sesquichlorohydrate and mixtures thereof.

The deodorant active agents may also be bacteriostatic agents or bactericides that act on underarm odor microorganisms, such as 2,4,4'-trichloro-2'-hydroxydiphenyl ether (®Triclosan), 2,4-dichloro-2'-hydroxydiphenyl ether, 3',4', 5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts, DPTA (1,3-diaminopropanetetraacetic acid), 1,2-decanediol (Symclariol from the company Symrise); glycerol derivatives, for instance caprylic/capric glycerides (Capmul MCM® from Abitec), glyceryl caprylate or caprate (Dermosoft GMCY® and Dermosoft GMC®, respectively from Straetmans), polyglyceryl-2 caprate (Dermosoft DGMC® from Straetmans), and biguanide derivatives, for instance polyhexamethylene biguanide salts; chlorhexidine and salts thereof; 4-phenyl-4,4-dimethyl-2-butanol (Symdeo MPP® from Symrise); zinc salts such as zinc salicylate, zinc gluconate, zinc pidolate, zinc sulfate, zinc chloride, zinc lactate or zinc phenolsulfonate; salicylic acid and derivatives thereof such as 5-n-octanoylsalicylic acid.

The deodorant active agents may be odor absorbers such as zinc ricinoleates, sodium bicarbonate; metallic or silver or silver-free zeolites, or cyclodextrins and derivatives thereof. They may also be chelating agents such as Dissolvine GL-47-S® from Akzo Nobel, EDTA and DPTA. They may also be a polyol such as glycerol or 1,3-propanediol (Zemea Propanediol sold by Dupont Tate and Lyle Bioproducts).

The deodorant active agents may also be enzyme inhibitors such as triethyl citrate or alum.

In the event of incompatibility and/or to stabilize them, for example, some of the active agents mentioned above may be incorporated into spherules, especially ionic or nonionic vesicles and/or nanoparticles (nanocapsules and/or nanospheres).

The deodorant active agents may be present in the cosmetic composition according to the invention in a concentration of from 0.01 to 15% by weight relative to the total weight of the composition.

Oily Phase

The compositions according to the invention contain at least one water-immiscible organic liquid phase, known as an oily phase. This phase generally comprises one or more hydrophobic compounds that make said phase water-immiscible. Said phase is liquid at ambient temperature (20-25° C.).

Preferentially, the oily phase is present in concentrations ranging from 1 to 50% by weight and more preferentially from 1 to 30% by weight relative to the total weight of the composition.

The oily phase of the anhydrous compositions in accordance with the invention comprises at least one volatile hydrocarbon-based oil.

The volatile hydrocarbon-based oil is chosen especially from hydrocarbon-based oils containing from 8 to 16 carbon atoms, and especially C8-C16 isoalkanes (also known as isoparaffins), for instance isododecane (also known as 2,2,4,4,6-pentamethylheptane), isodecane and isohexadecane, for example the oils sold under the trade names Isopar or Permethyl, branched C8-C16 esters and isohexyl neopentanoate, and mixtures thereof. Use may also be made of other volatile hydrocarbon-based oils, such as petroleum distillates, in particular those sold under the name Shell Solt by the company Shell; and volatile linear alkanes, such as those described in Patent Application DE10 2008 012 457 by the company Cognis.

Preferably, the volatile hydrocarbon-based oil is selected from C8-C16 isoalkanes and in particular from isododecane, isodecane, isohexadecane and mixtures thereof, and more particularly still isododecane.

Preferably, the volatile hydrocarbon-based oil or oils are present in concentrations ranging from 0.1 to 10% in weight and more preferably from 0.5 to 5% in weight relative to the total weight of the composition.

According to one particular embodiment of the invention, the oily phase of the anhydrous compositions in accordance with the invention comprises at least one additional oil.

The additional oil may be selected from mineral, plant or synthetic oils; in particular non-volatile hydrocarbon-based oils and/or volatile or non-volatile silicone oils, volatile or non-volatile fluoro oils, and mixtures thereof.

Preferably, the additional oil or oils are present in concentrations ranging from 0.1 to 99% and more preferably from 1 to 50% relative to the total weight of the oily phase.

The term "non-volatile oil" is intended to mean an oil that remains on the skin or the keratin fiber at ambient temperature and atmospheric pressure for at least several hours, and that especially has a vapor pressure of less than $10^{-3}$ mmHg (0.13 Pa).

The volatile silicones may be chosen from linear or cyclic volatile silicone oils, in particular those with a viscosity of 8 centistokes ($8 \times 10^{-6}$ m$^2$/s), and containing in particular from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane and mixtures thereof.

Mention may also be made of the volatile linear alkyltrisiloxane oils of general formula (I):

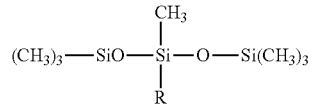

where R represents an alkyl group comprising from 2 to 4 carbon atoms, one or more hydrogen atoms of which can be substituted by a fluorine or chlorine atom.

Mention may be made, among the oils of general formula (I), of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

As examples of non-volatile oils that may be used in the invention, mention may be made of:
hydrocarbon-based oils of plant origin, such as coconut oil, sunflower oils, liquid triglycerides of fatty acids containing from 4 to 24 carbon atoms, for instance caprylic/capric acid triglycerides such as those sold by the company Stéarineries Dubois or those sold under the names Miglyol 810, 812 and 818 by the company Dynamit Nobel;

linear or branched hydrocarbons of mineral or synthetic origin, such as liquid paraffins and derivatives thereof, petroleum jelly, polydecenes, polybutenes, hydrogenated polyisobutene, such as Parleam, or squalane;

synthetic ethers containing from 10 to 40 carbon atoms, especially propylene glycols and derivatives thereof, such as PPG 14 butyl ether, synthetic esters, especially of fatty acids, such as isononyl isononanoate, isopropyl myristate, isopropyl palmitate, C12-C15 alcohol benzoate, hexyl laurate, diisopropyl adipate, 2-ethylhexyl palmitate, 2-octyldodecyl stearate, 2-octyldodecyl erucate, isostearyl isostearate;

fatty alcohols that are liquid at ambient temperature, containing a branched and/or unsaturated carbon-based chain containing from 12 to 26 carbon atoms, for instance octyldodecanol, isostearyl alcohol, 2-butyloctanol, 2-hexyldecanol, 2-undecylpentadecanol or oleyl alcohol;

higher fatty acids, such as oleic acid, linoleic acid or linolenic acid;

carbonates;

acetates;

citrates;

fluoro oils that are optionally partially hydrocarbon-based and/or silicone-based, for instance fluorosilicone oils, fluoropolyethers and fluorosilicones as described in the document EP-A-847 752;

silicone oils, for instance non-volatile polydimethylsiloxanes (PDMSs); phenyl silicones, for instance phenyl trimethicones, phenyl dimethicones, phenyl-trimethylsiloxydiphenylsiloxanes, diphenyl dimethicones, diphenylmethyl-diphenyltrisiloxanes, 2-phenylethyl trimethylsiloxysilicates, and mixtures thereof.

Preferably, use will be made of at least one additional oil selected from plant oils such as coconut oil and sunflower oil, synthetic esters of fatty acids, C10-C40 ethers such as PPG-14-butyl ether, non-volatile silicones and mixtures thereof and more preferably isopropyl palmitate, isononyl isononanoate, a polydimethylsiloxane (INCI name: Dimethicone) and mixtures thereof.

Preferably, the additional oil or oils are present in concentrations ranging from 0.1 to 90% and more preferably from 0.1 to 80% relative to the total weight of the oily phase.

Clay

Among the clays, mention may be made of clays of the smectite family, such as laponite, of the kaolinite family, such as kaolinite, dickite, nacrite, optionally modified clays of the halloysite, dombassite, antigorite, berthierine, pyrophyllite, montmorillonite, beidellite, vermiculite, talc, stevensite, hectorite, saponite, chlorite, sepiolite and illite family.

Clays are products that are already well known per se, which are described, for example, in the publication Minéralogie des argiles [Mineralogy of Clays], S. Caillère, S. Hénin, M. Rautureau, 2nd Edition 1982, Masson, the teaching of which is included herein by way of reference.

Natural clay is a sedimentary rock composed to a large extent of specific minerals, silicates generally of aluminium. Kaolin is thus a natural clay.

The clays may also be chemically modified by various compounds, such as acrylic acids, polysaccharides (for example carboxymethylcellulose) or organic cations such as quaternary ammonium compounds.

By way of natural clay, mention may be made of green clays, in particular rich in illite; clays rich in montmorillonite, known as fuller's earth, or such as bentonite or else white clays rich in kaolinite. As bentonites, mention may in particular be made of those sold under the names Bentone 38 VCG, Bentone Gel CAO V, Bentone 27 V and Bentone Gel MIO V by the company Elementis.

According to one particularly preferred embodiment, use will be made of a clay selected from hydrophobic modified bentonites and hydrophobic modified hectorites, in particular that are modified by a C10 to C22 quaternary ammonium chloride, such as:

a bentonite modified by stearalkonium chloride such as the commercial product sold under the name Tixogel MP 250 by the company Sud Chemie Rheologicals, United Catalysts Inc. (INCI name: Stearalkonium Bentonite);

a hectorite modified by distearyldimethylammonium chloride such as, for example, the product sold under the name Bentone 38V®, Bentone 38® or Bentone Gel® by the company Elementis (INCI name: Disteardimonium Hectorite), the hectorite modified by distearyldimethylammonium chloride in the presence of propylene carbonate (INCI name: Disteardimonium Hectorite (and) Propylene Carbonate such as the products Bentone Gel ISD V and Bentone Gel EUG V.

The clay or clays are present in the composition at concentrations ranging preferably from 0.1 to 5% by weight and more preferably from 0.1 to 1% relative to the total weight of the composition.

Propellant

The propellants are advantageously selected from dimethyl ether (DME), volatile hydrocarbons such as n-butane, propane, isobutane, and mixtures thereof, optionally with at least one chlorinated and/or fluorinated hydrocarbon. Among the latter, mention may be made of the compounds sold by the company DuPont de Nemours under the names Freon® and Dymel®, and in particular monofluorotrichloromethane, difluorodichloromethane, tetrafluorodichloroethane and 1,1-difluoroethane, sold especially under the trade name Dymel 152 A by the company DuPont. Carbon dioxide, nitrous oxide, nitrogen or compressed air may also be used as propellant.

The composition containing the deodorant active agent(s) and the propellant(s) may be in the same compartment or in different compartments in the container.

According to the invention, the concentration of propellant preferably ranges between 55% and 95% by weight relative to the total weight of the pressurized composition. More preferably, the concentration of propellant ranges from 70% to 90% by weight relative to the total weight of the pressurized composition.

The expression "pressurized composition" is understood to mean the total fluid+gas composition contained in the container.

Additives

The cosmetic compositions according to the invention may also comprise cosmetic adjuvants chosen from lipophilic suspension agents or gelling agents, softeners, antioxidants, opacifiers, stabilizers, moisturizers, vitamins, bactericides, preserving agents, polymers, fragrances, thickeners or suspending agents or any other ingredient usually used in cosmetics for this type of application.

Needless to say, a person skilled in the art will take care to select this or these optional additional compounds such that the advantageous properties intrinsically associated with the cosmetic composition in accordance with the invention are not, or are not substantially, adversely affected by the envisaged addition(s).

Suspension Agents/Gelling Agents

The antiperspirant composition according to the invention may also contain one or more suspension agents and/or one or more gelling agents. Some of them may perform both functions simultaneously.

Among the agents that may be used as suspension agents and/or lipophilic gelling agents, mention may be made of hydrotalcites, in particular hydrophobic-modified hydrotalcites, for instance the products sold under the name Gilugel by the company BK Giulini.

Mention may also be made of fumed silica optionally subjected to a hydrophobic surface treatment, the particle size of which is less than 1 µm. It is in fact possible to chemically modify the surface of the silica, by chemical reaction generating a reduced number of silanol groups present at the surface of the silica. It is possible in particular to replace silanol groups with hydrophobic groups: a hydrophobic silica is then obtained. The hydrophobic groups may be trimethylsiloxyl groups, which are obtained in particular by treatment of fumed silica in the presence of hexamethyldisilazane. Silicas thus treated are named "silica silylate" according to the CTFA (8th edition, 2000). They are sold, for example, under the references Aerosil R812® by the company Degussa, Cab-O-Sil TS-530® by the company Cabot. The hydrophobic groups may be dimethylsilyloxyl or polydimethylsiloxane groups, which are obtained especially by treating fumed silica in the presence of polydimethylsiloxane or dimethyldichlorosilane. Silicas thus treated are known as "silica dimethyl silylate" according to the CTFA (8th Edition, 2000). They are sold, for example, under the references Aerosil R972® and Aerosil R974® by the company Degussa, and Cab-O-Sil TS-610® and Cab-O-Sil TS-720® by the company Cabot.

The hydrophobic fumed silica in particular has a particle size that may be nanometric to micrometric, for example ranging from approximately 5 to 200 nm.

According to a particular embodiment of the invention, the suspension agents or gelling agents may be activated with oils such as propylene carbonate or triethyl citrate.

The amounts of these various constituents that may be present in the composition according to the invention are those conventionally used in compositions for treating perspiration.

The invention also relates to a method for the cosmetic treatment of human perspiration, and optionally of the body odors associated with human perspiration, which consists in applying to the surface of the skin an effective amount of the cosmetic composition as described previously.

The application time of the cosmetic composition on the surface of the skin may range from 0.5 to 10 seconds and preferably from 1 to 5 seconds.

The cosmetic composition in accordance with the invention may be applied several times to the surface of the skin.

In particular, the cosmetic treatment method according to the invention consists in applying to the surface of the armpits an effective amount of the cosmetic composition as described above.

The invention also relates to the use of said composition for the cosmetic treatment of human perspiration.

Another subject of the present invention is an aerosol device consisting of a container comprising an aerosol composition as defined previously and of a means for dispensing said composition.

The dispensing means, which forms a part of the aerosol device, generally consists of a dispensing valve controlled by a dispensing head, which itself comprises a nozzle via which the aerosol composition is vaporized. The container containing the pressurized composition may be opaque or transparent. It may be made of glass, polymer or metal, optionally coated with a protective varnish coat.

The examples which follow illustrate the present invention without limiting the scope thereof.

EXAMPLES 1A AND 1B

Example 1

Standard Fluid

| Ingredients | Quantity |
| --- | --- |
| ALUMINUM CHLOROHYDRATE (REACH 103 - SUMMITREHEIS) | 50 |
| DISTEARDIMONIUM HECTORITE (BENTONE 38 VCG - ELEMENTIS) | 2.6 |
| REFINED COCONUT OIL (GV 24/26 - SIO) | 10 |
| FRAGRANCE | 8.58 |
| ALPHA,OMEGA-DIHYDROXYL POLYDIMETHYLSILOXANE/5 CST POLYDIMETHYLSILOXANE MIXTURE (XIAMETER PMX-1503 FLUID - DOW CORNING) | 4.0 |
| PROPYLENE CARBONATE (JEFFSOL PROPYLENE CARBONATE-HUNTSMAN) | 0.87 |
| ISODODECANE | 15.0 |
| ISOPROPYL PALMITATE | qs 100 |

Preparation Method:

Placed in a beaker, under stirring, were isopropyl palmitate, coconut oil pre-melted at 50° C., the gum (alpha, omega-dihydroxyl polydimethylsiloxane/5 cst poly-dimethylsiloxane mixture). The hectorite was then incorporated and left for 5 minutes under stirring. Next the propylene carbonate was incorporated over 10 minutes. The fragrance, and then the aluminum salts were added under vigourous stirring. And finally the isododecane was added.

| Composition | Example 1A (invention) | Example 1B (outside the invention) |
| --- | --- | --- |
| Fluid | 14 | 14 |
| ISOBUTANE | 86 | 86 |

Example 1A (invention) corresponds to an aerosol device for dispensing each of the compositions 2 and 3, comprising:
i) a dispensing head (1) intended to be fitted on a container that contains each composition, comprising:
  a body (3) that is open at its two opposite axial ends,
  an engaging part (10) that is open at its two opposite axial ends, defining 10 holes.

Example 1B (outside the invention) corresponds to a conventional aerosol device from Precision APSL® 0.41 mm diameter direct outlet, in which a fluid described above is incorporated.

Comparative IN VITRO Tests

1) Whitening Test:

Protocol:

Applied to a glass plate was a support simulating the appearance of skin (SUPPLALE® support from Idemitsu)

of skin color. The aerosols were placed at a distance of 10 cm in order to simulate in vivo application. They were depressed for 2 seconds. The tests were repeated 3 times.
Results:
White appearance of the deposit;

| Aerosol device | White deposit |
| --- | --- |
| Example 1A (invention) | + |
| Example 1B (outside the invention) | +++ |

+ very slight white deposit
+++ sizeable white deposit

The aerosol device 1A in accordance with the present invention with the fluid from example 1 made it possible to obtain a very slight white deposit on the support simulating the appearance of skin, unlike the aerosol device 1B.

Drying Time Test:
Protocol:
Into an aluminum dish, each aerosol was sprayed after shaking for 10 seconds at a distance of 10 cm. The weight loss was measured at times of 30, 60 and 120 seconds on a Mettler precision balance. The greater the weight loss, the faster the drying and the evaporation of the solvents and volatile oils.
Results:

| Weight loss | 0 s | 30 s | 60 s |
| --- | --- | --- | --- |
| Example 1A (invention) | 0 | 0.43 g | 0.41 g |
| Example 1B (outside the invention) | 0 | 0.02 g | 0.04 g |

The aerosol device 1A in accordance with the present invention with the fluid from example 1 made it possible to obtain a faster drying of the formula tested relative to the aerosol device 1B.

Test of Tackiness and Greasiness:
Protocol:
Applied to a plate was a support simulating the appearance of skin (SUPPLALE® support from Idemitsu) of skin color. The aerosols were placed at a distance of 10 cm in order to simulate in vivo application. They were depressed for 2 seconds. The tests were repeated 3 times.

A panel made up of 10 people tested the tackiness of the system, after a drying time of 2 minutes, by application of the index finger. The people chose among the following sensory qualitative scores nos. 1, 2 or 3:

1—very tacky and greasy, with a large deposit on the finger
2—averagely tacky and slightly greasy, with a slight deposit on the finger
3—not tacky and not greasy, the finger is dry Results: the 10 people unanimously chose the following qualitative scores for each of the aerosol devices evaluated.

| Aerosol device + example 1 fluid | Qualitative scores |
| --- | --- |
| Example 1A (invention) | 1: very tacky and greasy, with a large deposit on the finger |
| Example 1B (outside the invention) | 3: not tacky and not greasy, the finger is dry |

Example 2

| Ingredients (INCI) | Example 2 fluid |
| --- | --- |
| DIMETHICONE 10 cst (BELSIL DM 10_WACKER) | — |
| DISTEARDIMONIUM HECTORITE (BENTONE 38 VCG - ELEMENTIS) | 2.6 |
| ISODODECANE | 10.5 |
| FRAGRANCE | 7 |
| PROPYLENE CARBONATE (JEFFSOL PROPYLENE CARBONATE- HUNTSMAN) | 0.87 |
| ALUMINUM SESQUICHLOROHYDRATE (REACH 301 - SUMMITREHEIS) | 15 |
| ALUMINUM CHLOROHYDRATE (REACH 103 - SUMMITREHEIS | 35 |
| ALPHA,OMEGA-DIHYDROXYL POLYDIMETHYLSILOXANE/5 CST POLYDIMETHYLSILOXANE MIXTURE (XIAMETER PMX-1503 FLUID - DOW CORNING) | 2.8 |
| REFINED COCONUT OIL (GV 24/26 - SIO) | 7 |
| ISOPROPYL PALMITATE | qs 100 |

| Composition | Example 2 |
| --- | --- |
| Fluid | 20 |
| ISOBUTANE | 80 |

Example 2 was prepared under the same conditions as example 1 with the same device as example 1A.

This device and this formula combine a three-fold benefit: care, efficacy and ease-of-use: does not sting, does not give a cold effect, gives a veil of softness to the skin, a soft and satiny film, while having a perception of efficacy.

The invention claimed is:

1. A device for dispensing a pressurized anhydrous composition, comprising:
   i) a dispensing head fitted on a container that contains said composition, comprising:
   a body that is open at its two opposite axial ends,
   an engaging part attached to the body that is open at its two opposite axial ends, comprising at least one dispensing orifice, the cross section of the at least one dispensing orifice along its transverse axis being between 0.02 mm$^2$ and 0.5 mm$^2$,
   ii) the pressurized anhydrous composition comprising:
   a) at least one oily phase comprising at least one volatile hydrocarbon-based oil,
   b) at least one clay, wherein the clay is selected from hydrophobically modified bentonites and hydrophobically modified hectorites,
   c) at least one deodorant active agent, and
   d) at least one propellant; and
   wherein the container is closed and/or pressurized.

2. The device as claimed in claim 1, the at least one dispensing orifice being annular shaped.

3. The device as claimed in claim 1, the at least one dispensing orifice having axial symmetry around the dispensing axis.

4. The device as claimed in claim 1, the at least one dispensing orifice having a triangular shaped cross section along its transverse axis.

5. The device as claimed in claim 1, the engaging part comprising a plurality of dispensing orifices, the sum of the cross sections of the dispensing orifices along its transverse axis being between 0.02 mm$^2$ and 0.5 mm$^2$.

6. The device as claimed in claim 4, the number of dispensing orifices being greater than or equal to 5.

7. The device as claimed in claim 1, the cross section of the at least one dispensing orifice along its transverse axis being between 0.03 mm$^2$ and 0.4 mm$^2$.

8. The device as claimed in claim 1, wherein the deodorant active agent is selected from antiperspirant active agents.

9. The device as claimed claim 1, wherein the at least one volatile hydrocarbon-based oil is present in concentrations ranging from 0.1% to 10% by weight relative to the total weight of the composition.

10. The device as claimed in claim 1, wherein the volatile hydrocarbon-based oil is selected from $C_8$-$C_{16}$ isoalkanes.

11. The device as claimed in claim 1, wherein the oily phase comprises at least one additional oil selected from non-volatile hydrocarbon-based oils, volatile silicone oils, non-volatile silicone oils, volatile fluoro oils, and non-volatile fluoro oils.

12. The device as claimed in claim 1, wherein the clay is modified by a $C_{10}$ to $C_{22}$ quaternary ammonium chloride.

13. The device as claimed in claim 2, wherein the at least one dispensing orifice has in the circumferential direction around the dispensing axis, a constant width (l).

14. The device as claimed in claim 1, the at least one dispensing orifice having rotational symmetry around the dispensing axis.

15. The device as claimed in claim 2, the at least one dispensing orifice having axial symmetry around the dispensing axis.

16. The device as claimed in claim 2, the cross section of at least one dispensing orifice along its transverse axis being between 0.03 mm$^2$ and 0.4 mm$^2$.

17. The device as claimed in claim 3, the cross section of the at least one dispensing orifice along its transverse axis being between 0.03 mm$^2$ and 0.4 mm$^2$.

18. The device as claimed in claim 4, the cross section of the at least one dispensing orifice along its transverse axis being between 0.03 mm$^2$ and 0.4 mm$^2$.

19. The device as claimed in claim 5, the cross section of the at least one dispensing orifice along its transverse axis being between 0.03 mm$^2$ and 0.4 mm$^2$.

20. The device as claimed claim 1, wherein the pressurized anhydrous composition comprises relative to the total weight of the composition from 1%-50% by weight of the at least one oily phase; from 0.1% to 10% by weight of the at least one volatile hydrocarbon-based oil; from 0.1% to 5% by weight of the at least one clay; from 0.01% to 15% by weight of the at least one deodorant active agent and from 55% to 95% by weight of the at least one propellant.

21. The device as claimed claim 1, wherein the pressurized anhydrous composition comprises relative to the total weight of the composition from 1% to 30% by weight of the at least one oily phase; from 0.5% to 5% by weight of the at least one volatile hydrocarbon-based oil; from 0.1% to 15% by weight of the at least one clay; from 0.01% to 15% by weight of the at least one deodorant active agent and from 70% to 90% by weight of the at least one propellant.

22. The device as claimed in claim 1, wherein the pressurized anhydrous composition further comprises propylene carbonate.

23. The device as claimed claim 1, wherein the pressurized anhydrous composition does not contain zinc pidolate.

24. The device as claimed in claim 1, wherein the volatile hydrocarbon-based oil is selected from $C_8$-$C_{16}$ isoalkanes; the clay is modified by a $C_{10}$ to $C_{22}$ quaternary ammonium chloride and the pressurized anhydrous composition further comprises propylene carbonate.

25. The device as claimed in claim 20, wherein the volatile hydrocarbon-based oil is selected from $C_8$-$C_{16}$ isoalkanes; the clay is modified by a $C_{10}$ to $C_{22}$ quaternary ammonium chloride and the pressurized anhydrous composition further comprises propylene carbonate.

26. A method for the cosmetic treatment of body odor and optionally of human perspiration, which comprises applying to the surface of human keratin material a composition dispensed by means of the dispensing device as claimed in claim 1.

* * * * *